US012589130B2

(12) United States Patent
Koumans et al.

(10) Patent No.: US 12,589,130 B2
(45) Date of Patent: Mar. 31, 2026

(54) *ALOE* EXTRACTS FOR MICROBIAL NEUTRALISATION

(71) Applicant: 2QR RESEARCH B.V., Delft (NL)

(72) Inventors: Floris Koumans, Delft (NL); Paul Kwakman, Mijdrecht (NL)

(73) Assignee: 2QR RESEARCH B.V., Delft (NL)

( * ) Notice: Subject to any disclaimer, the term of this patent is extended or adjusted under 35 U.S.C. 154(b) by 340 days.

(21) Appl. No.: 18/136,589

(22) Filed: Apr. 19, 2023

(65) Prior Publication Data

US 2023/0256046 A1     Aug. 17, 2023

Related U.S. Application Data

(63) Continuation of application No. PCT/EP2021/079228, filed on Oct. 21, 2021.

(30) Foreign Application Priority Data

Oct. 21, 2020   (EP) .................................... 20202957

(51) Int. Cl.
| | |
|---|---|
| *A61K 36/886* | (2006.01) |
| *A61K 47/26* | (2006.01) |
| *A61P 31/00* | (2006.01) |

(52) U.S. Cl.
CPC ............ *A61K 36/886* (2013.01); *A61K 47/26* (2013.01); *A61P 31/00* (2018.01)

(58) Field of Classification Search
CPC ........ A61K 36/886; A61K 47/26; A61P 31/00
See application file for complete search history.

(56) References Cited

U.S. PATENT DOCUMENTS

| | | | | |
|---|---|---|---|---|
| 7,288,270 B1 * | 10/2007 | Sekharam | .............. | A61K 36/82 |
| | | | | 424/725 |
| 2003/0096378 A1 * | 5/2003 | Qiu | ......................... | C12P 19/14 |
| | | | | 424/744 |
| 2004/0265344 A1 * | 12/2004 | Zolotariov | .............. | A61K 9/02 |
| | | | | 424/744 |
| 2016/0346436 A1 | 12/2016 | Boluk et al. | | |

FOREIGN PATENT DOCUMENTS

| | | |
|---|---|---|
| CN | 101724089 A | 6/2010 |
| EP | 1 323 738 A1 | 7/2003 |
| KR | 2017-0030689 A | 3/2017 |
| WO | WO 90/01253 A1 | 2/1990 |
| WO | WO 03/055918 A1 | 7/2003 |
| WO | WO 2006/056801 A1 | 6/2006 |
| WO | WO 2017/117500 A1 | 7/2017 |

OTHER PUBLICATIONS

WO, PCT/EP2021/079228 ISR and Written Opinion, Jan. 31, 2022.
(Continued)

*Primary Examiner* — Bethany P Barham
(74) *Attorney, Agent, or Firm* — ONE LLP

(57) ABSTRACT

The present invention relates to a composition comprising polysaccharides derivable from *Aloe vera* with aggregating activity towards microorganisms and to its use in preventing or treating infections. The composition having an average molecular weight in the range of 30-100 kDa and comprising 80-100% w/w mannose and 0-5% w/w glucose.

14 Claims, 1 Drawing Sheet

(56) References Cited

OTHER PUBLICATIONS

Chandrakar, S., et al., "Antibiotic Potential of Endophytic Actinomycetes of Medicinal Herbs Against Human Pathogenic Bacteria", Proc. Natl. Acad. Sci., India, Sect. B Biol. Sci., 2017, vol. 87, No. 3, pp. 905-915.

Roche, AM, "Antibody blocks acquisition of bacterial colonization through agglutination", Mucosal Immunology, 2015, vol. 8, No. 1, pp. 176-185.

Vu, T. T., et al., "Acemannan Used as an Implantable Biomaterial for Vital Pulp Therapy of Immature Permanent Teeth Induced Continued Root Formation", Pharmaceutics, 2020, vol. 12, No. 7, pp. 1-15.

JP, 2023-549003 Office Action, Jul. 23, 2025.

* cited by examiner

ALOE EXTRACTS FOR MICROBIAL NEUTRALISATION

CROSS-REFERENCE TO RELATED APPLICATIONS

This application is a continuation of International Patent Application No. PCT/EP2021/079228, filed Oct. 21, 2021, which claims priority to European Patent Application No. 20202957.5, filed on Oct. 21, 2020, both of which are herein expressly incorporated by reference in their entireties for all purposes.

FIELD OF THE INVENTION

The present invention relates to *Aloe* extracts for microbial neutralisation. In particular, it relates to *Aloe* extracts which promote microbial neutralisation by promoting aggregation of microorganisms.

BACKGROUND OF THE INVENTION

Pathogenic microorganisms have developed tools to breach the natural host defence system to colonize and invade our tissues. The majority of microbial problems are initiated by the adhesion of harmful microorganisms to human epithelial surfaces, such as skin and mucosa. To effectively bind to host tissue surfaces, many microorganisms possess multiple adhesin proteins on their outer surface. These adhesins bind to receptor molecules at the surface of host epithelial cells. Anti-adhesive strategies are aimed at blocking the interaction between microbial adhesins and host epithelial cell receptors by blocking these receptors in order to prevent microbial colonisation of host cells. Since microbial colonisation is the first crucial step in the process of infection, effectively blocking microbial adhesion by anti-adhesive strategies renders pathogens harmless. However, a draw back of anti-adhesion therapy is that most pathogenic microorganisms possess genes encoding more than one type of adhesin protein. As a result, blocking of each of those adhesin proteins is necessary for successful blocking.

Colonisation may also be counteracted by microbial aggregation, also referred to as clustering. Aggregation is a process where microorganisms are entangled in a network by means of aggregating compounds that form crosslinks between those individual microorganisms. Aggregating factors have been described. Roche et al. 2015 Mucosal Immunol. 8:176 describes how antibodies play a major role in the defence against colonization and infection due to the physical process of aggregation of microorganisms by antibodies. WO2017/117500 describes oral compositions comprising mucin-coated silica for promoting bacterial aggregation and clearance thereof from the oral cavity. US2016/346436 describes a method of inducing bacterial aggregation comprising contacting bacteria with nanocrystalline cellulose (NCC) or with a NCC hydrogel composition, thereby causing aggregation and thereby reducing the ability of the bacteria to adhere to a surface or forming a biofilm.

Extracts from *Aloe vera* have been used for their medicinal properties. Vu et al. Pharmaceutics (2020) 12:644 discloses an *Aloe vera* extract composed of 57-77% mannose, 15-22% glucose and 5-7% galactose and a molecular weight of 150-800 kDa. This extract is formulated into sponges for dental use to stimulate pulp tissue generation. EP 1 323 738 describes a negatively charged *Aloe vera* polysaccharide fraction comprising 0-40% glucose and 60-100% mannose.

The polysaccharides in this fraction have a molecular weight between 100 and 300 kDa and block adhesion of bacteria to tissue. Known antimicrobial agents from *Aloe vera* are based on anti-adhesion and are unlikely to block each and every microbial adhesion protein. Aggregating factors from *Aloe vera* have not been disclosed so far.

DETAILED DESCRIPTION OF THE INVENTION

Figure 1A:
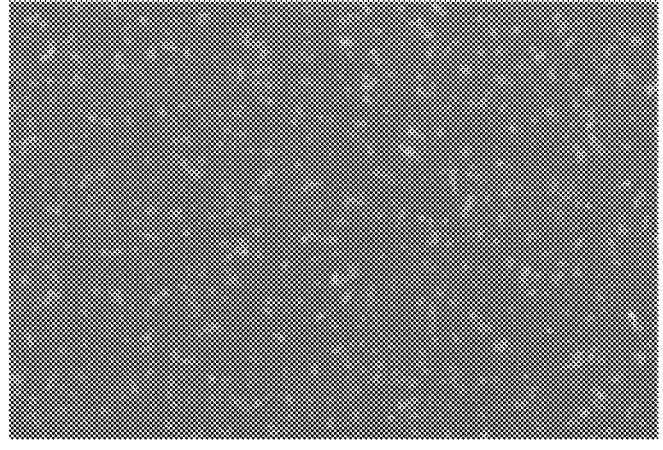
FIG. 1A Aggregation of FITC-stained *S. aureus* by neutral IEX fraction DO.

In one aspect, the present invention relates to a composition with aggregating activity towards microorganisms. The composition comprises polysaccharides derivable from *Aloe vera*.

One advantage of the composition according to the invention is that it has aggregating activity to microorganisms, whereby it immobilizes the microorganisms in aggregates or clusters. These aggregates neutralise the microorganisms. One reason being that because the micro-organisms form clusters, they have less anti-adhesive capacity. Due to a greatly reduced adhesive cell membrane surface, less surface is available for adhesion to host epithelium when micro-organisms are aggregated in clusters. Aggregates may more easily be cleared from an individual's body than a single microorganism. The aggregating effect thus supports the natural defence mechanism of the epithelium against microbial invasion. Another advantage is that bacteria are not killed and therefore antimicrobial resistance is not induced. Yet another advantage is that the composition according to the invention may be used for aggregation of a wide range of different microorganisms. Both bacteria, fungi (including yeast) and viruses may be aggregated.

In one embodiment, the microorganism is a Gram negative bacterium, a Gram positive bacterium or a fungus. Suitable examples of bacteria or fungi which may be aggregated include those selected from the group consisting of *Bacillus, Bacteroides, Clostridium, Enterococcus, Escherichia, Listeria, Neisseria, Pseudomonas, Salmonella, Staphylococcus, Streptococcus, Yersinia, Aspergillus* and *Candida*. In a preferred embodiment, the microorganism is selected from the group consisting of *Candida. Enterococcus, Escherichia, Helicobacter, Klebsiella, Lactobacillus, Propionobacterium, Staphylococcus* or *Streptococcus*. In one embodiment, the microorganism to be aggregated is selected from the group consisting of *Candida albicans, Staphylococcus aureus, Escherichia coli* and *Helicobacter pylori*. In another embodiment, the microorganism is selected from the group consisting of *E. coli* ATCC 25922, *Enterococcus faecalis, Candida albicans* ATCC 10231, *Klebsiella pneumoniae. Lactobacillus* crispatus DSMZ 20584, *Lactobacillus* gasseri DSMZ 20243, *Lactobacillus rhamnosus, Propionobacterium acnes, Streptococcus mitis* and *Streptococcus pyogenes*. In another embodiment, the microorganism is *Staphylococcus aureus* ATCC 35556, *S. aureus* genotype B (GTB), vancomycin resistant *S. aureus*, methicillin-resistant *S. aureus* or multi-resistant *S. aureus*.

In one embodiment, a composition according to the invention is obtained from *Aloe*, in particular from *Aloe vera*, also known as *Aloe barbadensis* Miller or *Aloe curacao*. The composition according to the invention may also be obtained from other *Aloe* species, including *Aloe arbore-scens, Aloe vahombe, Aloe ferox* and *Aloe Saponaria*. The composition may be obtained from the *Aloe* inner leaf fillet, which is the clear gel in the *Aloe* leaf. In one embodiment, the composition is obtained from *Aloe* inner leaf fillet containing not less than 10% w/w polysaccharides after lyophilization of the gel. The composition may be decolorized.

The composition according to the invention may also be obtained from other plants, such as from *Vaccinium macro-carpon* (Cranberry), *Panax ginseng, Plantago, Echinacea, Garcinia, Arnica, Angelica, Hibiscus, Glycyrrhiza* and Moringa.

Preferably, the composition is uncharged at pH 7. The composition does not bind to, and ends up in the flow through of, an anion-exchange column like Q-Sepharose at pH 7.

The composition according to the invention may comprise or consist of polysaccharides having an apparent molecular weight in the range of 30-100 kDa or >1000 kDa. Preferably, a composition according to the invention comprises or consists of polysaccharides having an apparent molecular weight in the range of 50-100 kDa. In one embodiment, the polysaccharides in the composition according to the invention have an apparent molecular weight in the range of 30-100 kDa, preferably in the range of 50-100 kDa. In another embodiment, the polysaccharides in the composition according to the invention have an apparent molecular weight of >1000 kDa. These fractions show aggregating activity towards microorganisms, such as towards *S. aureus* or *E. coli*. Apparent molecular weight may be determined by methods known in the art, e.g. ultrafiltration.

As shown in the Examples below; the composition according to the invention differs from acemannan, which comprises relatively less mannose and more glucose. Acemannan is preferably prepared by ethanol precipitation. In one embodiment, acemannan is prepared by adding 4 parts of 96% ethanol to one part of *Aloe* juice, mixing the mixture and incubating it without stirring for at least 4 hours and maximally 24 hours to allow for precipitation of polysaccharides, centrifuging the mixture for 15 min. at >3500×g and recovering the pellet containing the precipitated polysaccharides. The pellet may be dried, e.g. by freeze-drying, and dissolved in an aqueous solution, preferably milliQ water.

Weight figures mentioned in this application are preferably based on dry weight, unless otherwise indicated.

The polysaccharide distribution in the composition according the invention is 80-100% w/w mannose and 0-5% w/w glucose, preferably 90-98% mannose and 0-5% w/w glucose, by weight of total polysaccharides. In one embodiment, the polysaccharide distribution in the composition according the invention is 85-95% w/w mannose, 3-4% w/w glucose by weight of total polysaccharides. In another embodiment, the polysaccharide distribution in the composition according the invention is 90-98% w/w mannose and 2-4% w/w glucose by weight of total polysaccharides.

The polysaccharides may further comprise 0)-5% w/w galactose and 0-5% w/w fucose, such as 1.0-5.0% w/w or 2.5-5% w/w, by weight of total polysaccharides.

Preferably, the polysaccharides in the composition do not comprise or comprise very little negatively charged polysaccharides, such as galacturonic acid or glucuronic acid, for example from 0)-3% w/w of total polysaccharides in the composition.

Preferably, the composition does not comprise or comprises very little anthraquinones, for example less than about 0.05% w/w or less than about 0.001% w/w.

In one embodiment, the polysaccharide distribution in the composition according the invention is 85-95% w/w mannose, 3-4% w/w glucose, 0-5% w/w galactose and 0)-1.5% w/w fucose, by weight of total polysaccharides. In another embodiment, the polysaccharide distribution in the composition according the invention is 90-98% w/w mannose and 2-4% w/w glucose, 0-5% w/w galactose and 0-1.5% w/w fucose, by weight of total polysaccharides.

Preferably, the polysaccharides in the composition comprise mannose:glucose in a weight ratio in the range of 25 to 35.

The polysaccharide content of the composition according to the invention is preferably at least 0.5 mg/ml, at least 1.0 mg/ml or at least 2.0 mg/ml, such as in the range of 0.5 mg/ml to 10 mg/ml, in the range of 1.0 mg/ml to 10 mg/ml, in the range of 1.0 mg/ml to 5.0 mg/ml, or in the range of 1.0 mg/ml to 3.5 mg/ml.

The mannose content of the composition according to the invention is preferably at least 0.5 mg/ml, at least 1.0 mg/ml or at least 2.0 mg/ml, such as in the range of 0.5 mg/ml to 10 mg/ml, in the range of 1.0 mg/ml to 10 mg/ml, in the range of 1.0 mg/ml to 5.0 mg/ml or in the range of 1.0 mg/ml to 3.5 mg/ml.

The galactose content of the composition according to the invention is preferably maximally 0.15 mg/ml, more preferably maximally 0.10 mg/ml.

The composition according to the invention may comprise or consist of polysaccharides having an apparent molecular weight in the range of 30-100 kDa or >1000 kDa, preferably in the range of 50-100 kDa, the polysaccharides comprising 80-100% w/w or 90-98% w/w mannose and 0-5% w/w glucose, by weight of total polysaccharides.

In one embodiment, the composition according to the invention, preferably being uncharged at pH 7, comprises 0.5 mg/ml to 10 mg/ml, in the range of 1.0 mg/ml to 10 mg/ml, in the range of 1.0 mg/ml to 5.0 mg/ml or in the range of 1.0 mg/ml to 3.5 mg/ml, polysaccharides having an apparent molecular weight in the range of 30-100 kDa or >1000 kDa, preferably in the range of 50-100 kDa, and the polysaccharides comprising 80-100% w/w or 90-98% w/w mannose and 0-5% w/w glucose, by weight of total polysaccharides.

In one embodiment, the composition, preferably being uncharged at pH 7, comprises from 0.01-100% w/w polysaccharides, such as 0.05-100% w/w, 40-80% w/w, 0.01-30% w/w, 5-80% w/w, 5-50% w/w; 10-30% w/w; 0.05-10% w/w, 0.05-1.0% w/w or 0.1-1.0% w/w; by weight of the composition, the polysaccharides having an apparent molecular weight in the range of 30-100 kDa or >1000 kDa, preferably in the range of 50-100 kDa, and the polysaccharides comprising 80-100% w/w or 90-98% w/w mannose and 0-5% w/w glucose, by weight of total polysaccharides.

In another embodiment, the composition, preferably being uncharged at pH 7, comprises 0.1-3% w/w polysaccharides having an apparent molecular weight of >1000 kDa, the polysaccharides comprising 80-100% w/w or 90-98% w/w mannose and 0-5% w/w glucose.

In yet another embodiment, the composition, preferably being uncharged at pH 7, comprises 0.05-0.5% w/w polysaccharides having an apparent molecular weight in the range of 30-100 kDa, preferably in the range of 50-100 kDa, the polysaccharides comprising 80-100% w/w or 90-98% w/w mannose and 0-5% w/w glucose, by weight of total polysaccharides.

The composition according to the invention may further comprise a carrier, such as a pharmaceutically-acceptable carrier.

The aggregating capacity of the composition for a microorganism may be expressed in Minimal Aggregation Concentration (MAC), which is the lowest concentration of polysaccharides of a sample which still convincingly shows microbial aggregation. In one embodiment, MAC is determined in a 2-fold dilution series. The lower the MAC, the more potent the composition. The composition preferably has a MAC of less than 8 mg polysaccharides/ml sample, less than 5 mg/ml, less than 2 mg/ml, less than 0.1 mg/ml, less than 0.01 mg/ml, less than 0.005 mg/ml, less than 0.003 mg/ml or less than 0.001 mg/ml, such as between 0.001 mg/ml and 7 mg/ml, between 0.001 mg/ml and 5 mg/ml, between 0.001 mg/ml and 1 mg/ml, between 0.001 mg/ml and 0.1 mg/ml, between 0.001 mg/ml and 0.010 mg/ml, between 0.001 mg/ml and 0.005 mg/ml, between 0.001 mg/ml and 0.003 mg/ml or between 0.001 mg/ml and 0.002 mg/ml, preferably when tested towards *S. aureus* ATCC 35556. This is preferably tested in a suitable assay, such as a fluorescence assay.

Quantification of polysaccharides may be by any suitable means, such as by dry weight determination, for example using freeze drying, or by hydrolysis of polysaccharides followed by subsequent chromatography, for example HPAEC-PAD.

Maximal Aggregating Dilution (MAD), the highest dilution of sample still showing aggregation may be determined by 2-fold serial dilutions, for example with PBS, with an equal amount of microorganism sample. In one embodiment according to the invention, the MAD value of a composition according to the invention is at least 100, at least 500 or at least 1000, such as between 100 and 2000, between 500 and 2000 or between 1000 and 2000, preferably when tested against *S. aureus* ATCC 35556.

In one embodiment, the composition according to the invention has a MAC of between 0.001 mg/ml and 0.010 mg/ml, between 0.001 mg/ml and 0.005 mg/ml, between 0.001 mg/ml and 0.003 mg/ml or between 0.001 mg/ml and 0.002 mg/ml and a MAD value of between 500 and 2000 or between 1000 and 2000, preferably when tested against *S. aureus* ATCC 35556.

The composition according to the invention is typically an aqueous liquid when isolated. It may be stored in any form. In one embodiment, it is stored in solid form, or example as a freeze dried powder. In another embodiment, it is stored in liquid form, for example as an aqueous liquid or gel.

In another aspect, the invention relates to a method for aggregating microorganisms to prevent infection or colonisation in particular colonisation of mucous layers, and to promote neutralisation of microorganisms in a subject's body. The subject may be a human, in particular people on medication, elderly or women. The subject may be an animal, in particular a mammalian animal, such as livestock, sports animals or pets, including cats, cattle, dogs, equine animals, fish, goats, poultry, rabbits, sheep, swine and sheep. The method comprises contacting the microorganism with a composition according to the invention. In one embodiment, the composition according to the invention is used in a method to prevent or treat mastitis in cattle, e.g. by formulating it into a gel and applying it in or to the udder. Mastitis is an inflammation of the udder, typically caused by bacteria, such as *E. coli*, Staphylococci or Streptococci, in particular, *Staphylococcus aureus*, *Streptococcus uberis*, *Streptococcus dysgalactiae* (SDY) or *Streptococcus agalactiae* (SAG). Mastitis may be subclinical, with no symptoms, or it may be clinical, with symptoms like udder swelling or udder redness or milk clotting or milk flaking. Mastitis symptoms may be mild or moderate or severe. In a preferred embodiment, the method is used for preventing or inhibiting mild or moderate mastitis in dairy cattle such as cows, goats or sheep, in particular, mild or moderate mastitis in cows. The traditional method for treating mastitis is an antibiotic treatment for 3-4 days, followed by a wash-out period of 3-4 days, to remove the antibiotics. The antibiotic is typically supplied by an udder injector for injection of the antibiotic in one or more teats of the udder. The effect of the antibiotics is limited. About 40% of the cattle shows a recurrency of mastitis after one week. Using a composition according to the invention, a better treatment is possible. In one embodiment, a gel comprising 1-3 gram/l polysaccharides, preferably about 2-3 gram/l polysaccharides, is used to treat mastitis, preferably mastitis involving *Staphylococcus*, in particular mastitis involving *S. aureus*. A suitable gel is a gel based on acrylic acid polymers (carbopol).

In another embodiment, the composition according to the invention is used in a method to prevent or treat metritis in cattle, e.g. by flushing the uterus of the animal with a gel according to the invention comprising 0.5-2 gram/l polysaccharides, preferably about 1-2 gram/l polysaccharides. The gel may further comprise a diluent, such as physiological saline, to allow for ample volume for flushing the uterus, and gelling agents, for example 2-4% w/w xanthan gum, to prevent immediate leaking from the uterus.

The composition according to the invention has aggregating activity towards microorganisms, which means that microorganisms aggregate when contacted with a composition according to the invention. This may be tested and visualized by labelling microorganisms with a suitable dye, for example a fluorescent dye, such as fluorescein isothiocyanate (FITC), Hoechst 33342, carboxyfluorescein succinimidyl ester (CFSE) or green fluorescent nucleic acid stain SYTO-24, which are all commercially available. Depending on the aggregating activity, dilution and microorganisms, aggregation may start immediately, within I second, within 1 minute, within 5 minutes, within 10 minutes, within 15 minutes, within 30 minutes, within one hour, within 2 hours or within 3 hours after contact between microorganisms and the composition according to the invention.

Aggregating activity may be apparent from clusters of microorganisms becoming visible, instead of single cells. Aggregation is usually sufficiently stable to delay examination of aggregation and may still be observed at least 3 hours, at least 4 hours, at least 5 hours or at least 16 hours, at least 18 hours or at least 24 hours after contacting microorganisms with the composition according to the invention. In one embodiment, aggregates may still be observed 5-16 hours, 5-24 hours or 5-48 hours after contacting microorganisms with the composition according to the invention.

In one embodiment, aggregation in a fluorescence assay is effected with a composition having a polysaccharide content between 0.001 mg/ml and 7 mg/ml, between 0.001 mg/ml and 5 mg/ml, between 0.001 mg/ml and 1 mg/ml, between 0.001 mg/ml and 0.1 mg/ml, between 0.001 mg/ml and 0.010 mg/ml, between 0.001 mg/ml and 0.005 mg/ml, between 0.001 mg/ml and 0.003 mg/ml or between 0.001 mg/ml and 0.002 mg/ml, preferably when tested towards *S. aureus* ATCC 35556.

In another aspect, the present invention relates to the use of the composition according to the invention. The composition may be used in or as food supplement or in dietary foods. The composition according to the invention may also be used in personal care or in cosmetics e.g. in dental care, ear care, eye care, hair care, nose care, skin care or vaginal care. In one embodiment, the composition is used in dental care in a toothpaste to prevent or treat gingivitis or caries. In another embodiment, the composition is used in eye care to protect eye lenses against colonisation of microorganisms.

The composition according to the invention may also be applied in pharmaceutical use, especially as a medicament or adjuvant in a pharmaceutical composition or in a method to prevent or treat infections with infectious microorganisms like bacteria, fungi (including yeast) or viruses. Infection refers to the invasion or multiplication of microorganisms which are not normally present within an individual's body or which are present in abnormal amounts. Such infectious microorganisms may also be referred to as pathogens.

An infection may be subclinical, without symptoms, or it may be clinically, with apparent symptoms. The effect of treatment or prevention may be permanent or temporary, such as for several days, several weeks, several months or several years. It may be complete or partial, such as immobilising some or all microorganisms. This may lead to prevention or reduction of invasion or multiplication of some or all microorganisms. In one embodiment, 5% to 100% or 5% to 60% or 60% to 100% of the microorganisms is immobilised.

The composition may be used in a release-coating to prevent colonisation of or biofilm formation on living surfaces or inert surfaces. To this end, surfaces may be coated with a composition according to the invention for immediate or controlled release. The composition causes aggregation of microorganisms on the coating and thus prevents colonization of or biofilm formation on the surface. When the coating is released, microorganisms aggregated on the coating are also released in aggregated form and can be easily removed from the body. Surfaces which may be treated this way include surfaces from medical devices, particularly indwelling medical devices, such as catheters, cardiac implantable electronic devices (CIED), heart valves, immobilizers, joint replacements, stents, tracheostomies and wound drains. The devices may comprise or consist of metal, ceramics or non-biodegradable synthetic polymers, like plastics or polytetrafluoroethylene (PTFE, Teflon (trademark)), or biodegradable polymers, like collagen, hyaluronic acid, polylactic acid or polyurethane. The medical devices are preferably indwelling devices or implants, which are meant to stay in the body for several days, weeks, months or years.

The composition may be applied topically, e.g. as a cream, drops, gel, liquid, lotion, paste, shampoo, spray or tonic. The composition may be applied orally. The composition may be dried, e.g. by spray drying or freeze drying, and formulated in an appropriate form, e.g. into a capsule, a lozenge, a powder or a tablet, preferably using suitable excipients. Excipients should be generally safe and non-toxic and acceptable for use, in particular for human or veterinary use.

The composition according to the invention may be used in combination with other compounds, such as other aggregating agents, such as nanocrystalline cellulose or silica: gelling agents or viscosifiers, such as chitosan, caprylyl glycol, 1,2 propylene glycol or xanthan gum; anti-microbials, such as antibiotics; vitamins, such as vitamin A, a vitamin B, vitamin D or vitamin E: minerals, such as calcium, zinc, iron or potassium. The skilled person will understand that one compound may have several different functions. For example, a vitamin may also be an antimicrobial. In one embodiment, the composition is used in combination with (other) *Aloe vera* extracts, antibiotics, chitosan, nutrients or vitamins. In another embodiment, the composition is combined with a viscous aqueous carrier for uterine for vaginal flushing. The other compound may be in the composition or separate, the other compound and the composition may be in the same formulation or in separate formulations. Separate formulations may be administered simultaneously or sequentially to an individual.

The skilled person will understand that the concentration of the composition in formulations may vary and will depend on factors such as formulation, site of application, use, age, sex and weight of a subject. In one embodiment, a formulation comprises between 2.0 ml/l and 800 ml/l of the composition according to the invention, such as between 50 ml/l and 800 ml/l, 100 ml/l and 800 ml/l, 200 ml/l and 800 ml/l or 400 ml/l and 800 ml/l.

In another embodiment, a composition according to the invention is formulated resulting in a polysaccharide concentration in the formulation of between 0.05 mg/ml and 10 mg/ml, between 0.5 mg/ml and 10 mg/ml or between 0.8 mg/ml and 5 mg/ml.

The skilled person will understand that also the dosage of the formulation comprising the composition according to the invention may vary and will depend on factors such as formulation, site of application, use, age, sex and weight of a subject. In one embodiment, a formulation comprising a composition according to the invention is dosed at between 0.01 and 10 mg polysaccharides/kg body weight, such as at 0.1-10 mg/kg body weight, 0.5-5.0 mg/kg body weight or 1-2 mg/kg body weight.

The formulation optionally comprises a pharmaceutically-acceptable excipient, such as an anti-adherent, antioxidant, binder, bulking agent, carrier, colourant, disintegrant, diluent, filler, flavour, lubricant, preserving agent, solvent, surfactant, sweetener, vehicle or wetting agent. The excipient should not adversely affect the stability of the composition in the formulation. The term "pharmaceutically acceptable" refers to suitable for preparing a pharmaceutical composition, such as generally considered safe and non-toxic.

EXAMPLES

Materials & Methods

Acemannan Preparation

Four parts of 96% ethanol were added to one part of B21 *aloe* juice, mixed and incubated without stirring for approximately 4 hours to allow for precipitation of polysaccharides. Subsequently, sample was centrifuged for 15 min. at >3500×g and supernatant was discarded. The pellet containing the precipitated polysaccharides was dried by freeze-drying, and dissolved in either milliQ water or another aqueous solution.

Aggregation

Microbial cells were fluorescently labelled with fluorescein isothiocyanate (FITC, Sigma-Aldrich, St Louis, MO, USA) or SYTO™ 24 green fluorescent nucleic acid stain (Thermo Fisher, Rockford, IL, USA). FITC labelling was performed by incubation in a 0.2 M NaHCO3 pH 9.5 buffer with a final concentration of 0.2 mg/ml FITC (from a 2 mg/ml FITC stock in DMSO) and shaking for 1 hour at 37° C. and subsequently extensively washing with phosphate buffered saline (PBS). SYTO-24 labelling was performed in PBS using a final 1 µM concentration of the dye for at least 30 minutes and subsequently washing with PBS. Fluorescently labelled microorganisms were incubated in PBS in flat-bottom polystyrene 96 wells plates or on a glass microscope slide in the absence or presence of *Aloe* sample or control. Labelled microbial samples were optionally diluted, for example to OD 0.1 or 0.2 before use. Aggregation was examined immediately or at a more convenient moment using a fluorescence microscope. If aggregation was not examined immediately, mixtures were stored at 4° C. until examination. Aggregation was apparent from clustering of fluorescently labelled microorganisms.

Maximal Aggregating Dilution (MAD)

Maximal Aggregating Dilution (MAD), the highest dilution of sample still showing aggregation, was determined by 2-fold serial dilutions, for example with PBS, with an equal amount of microorganism sample.

Minimal Aggregating Concentration (MAC)

The Minimal Aggregation Concentration (MAC), the lowest concentration of polysaccharides still convincingly showing microbial aggregation, was determined by 2-fold serial dilutions and expressed in mg or microgram polysaccharides/ml. The lower the MAC, the more potent the aggregating activity for a microorganism. Quantification of samples was based on dry weight determination unless otherwise indicated.

Example 1 Aggregation Activity in *Aloe vera*

10× concentrated *Aloe vera* leaf juice, a 10× decolorized liquid made from purified inner leaf fillet that contained not less than 10% polysaccharides, was purchased at a commercial supplier (ACTIValoe® *Aloe vera* Gel 10X-D, AloeCorp, Harlingen, TX, USA). This material was dialyzed against demi water with a Spectra/Por 4 RC Dialysis Membrane Tubing 12-14 kDa MWCO dialysis membrane (Spectrum Medical Industries Inc., Los Angeles, USA) to remove all <10 kDa components. The aggregating activity of the juice fractions towards *Staphylococcus aureus* was determined as described under Materials & Methods above. Aggregating activity was present in the >12 kDa fraction. The Minimal Aggregation Concentration (MAC) of the >12 kDa fraction was determined and compared to that of D-mannose. The results are presented in Table 1. D-mannose did not have aggregating activity at the highest concentration tested (16 mg/ml), while 4 times diluted >12 kDa fraction of *Aloe vera* inner leaf juice containing less than 1.28 mg/ml polysaccharides still showed aggregation and could have been diluted even further while keeping aggregating activity.

TABLE 1

|  | MAC (mg/ml) |
| --- | --- |
| D-mannose (control) | >16 |
| *Aloe vera* inner leaf juice MWCO >12 kDa | <1.28 |

Example 2 Aggregation of Microorganisms

The aggregation capacity of the >12 kDa fraction of Example 1 was tested with various microorganisms. Maximal Aggregating Dilution (MAD) results are shown in Table 2 and show that a wide range of microorganisms ranging from Gram-positive bacteria, Gram-negative bacteria to yeast, including some pathogens, could be aggregated by the >12 kDa fraction.

TABLE 2

| Microorganism | MAD of >12 kDa fraction |
| --- | --- |
| *Candida albicans* ATCC 10231 | ++ |
| *Staphylococcus aureus* ATCC 35556 | +++ |
| *Lactobacillus gasseri* DSMZ 20243 | +++ |
| *Staphylococcus capitis* | +++ |
| *Lactobacillus rhamnosus* | + |
| *Lactobacillus crispatus* DSMZ 20584 | + |
| *Klebsiella pneumoniae* | + |
| *Streptococcus pyogenes* | ++ |
| *Enterococcus faecalis* | + |
| *E. coli* ATCC 25922 | ++ |
| *Propionibacterium acnes* | +++ |
| *Streptococcus mitis* | +++ |

+ between 2× and 64×;
++ between 128× and 512×;
+++ at least 1000×

Example 3 IEX Characterization of *Aloe* Extract

To further characterise the fraction responsible for *A. vera* aggregating activity towards microorganisms, 10× concentrated *Aloe vera* inner leaf juice (ACTIValoe®) *Aloe Vera* Gel 10X-D, AloeCorp, Harlingen, TX, USA) was dialyzed against demi water with a Spectra Por 4 RC Dialysis Membrane Tubing 12-14 kDa MWCO dialysis membrane (Spectrum Medical Industries Inc., Los Angeles, CA) to remove all <10 kDa components. The dialyzed material was subsequently reconstituted in a 20 mM NaPO4 pH 7.0 buffer and was manually loaded onto a Q Sepharose FastFlow column (GE Healthcare, Uppsala, Sweden) and separated using a batch-wise procedure. Two ion-exchange (IEX) fractions were collected. First, the uncharged flow through in 20 mM NaPO4 buffer pH7 was collected (D0 fraction). Subsequently, negatively-charged compounds were eluted with a 20 mM NaPO$_4$/0.5 M NaCl buffer pH7 (DI fraction). Elution of polysaccharides was measured using refractive index detection. Fractions containing polysaccharides were pooled, dialyzed against a 12-14 kDa MWCO dialysis membrane, precipitated in 80% ethanol (overnight incubated at −20° C. and centrifuged at 3000×g for 20 min) and subsequently freeze-dried. The yield of polysaccharides was determined, based on dry weight. The D0 fraction comprised 97% of the polysaccharides in the *A. vera* inner leaf juice and the D1 fraction comprised 3% of the polysaccharides.

Figure 1B:
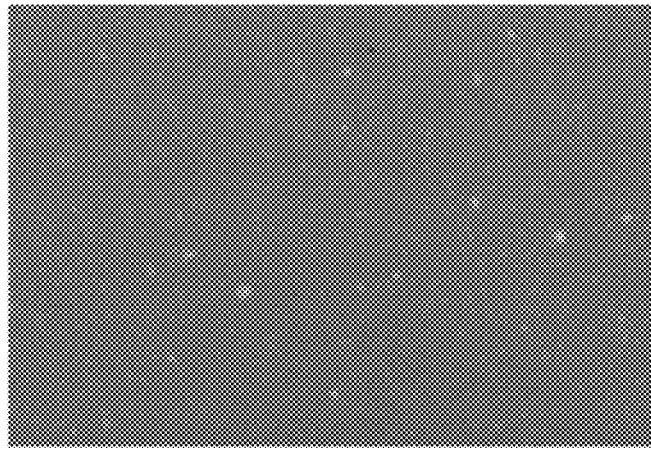
FIG. 1B Lack of aggregation of FITC-stained *S. aureus* by negatively charged IEX fraction DI.

D0 and D1 were incubated in phosphate buffered saline (PBS), both at a concentration of 2 mg/ml, with FITC-labelled *S. aureus* cells at an OD of 0.2 in a transparent, flat-bottom polystyrene 96 wells plate (Greiner Bio-One, Monroe, NC) at room temperature without shaking. Within 10 minutes after addition of D0, the *S. aureus* bacteria started to aggregate (FIG. 1A). Incubation with the D1 fraction did not lead to aggregation (FIG. 1B). This shows that the D0 fraction is responsible for the aggregating activity of *A. vera* inner leaf juice.

Example 4 Aggregation Activity Towards *S. aureus* and *H. pylori*

To further characterise the fraction responsible for *A. vera* aggregating activity towards microorganisms, 10× concentrated *Aloe vera* inner leaf juice (ACTIValoe® *Aloe Vera* Gel 10X-D, AloeCorp, Harlingen, TX, USA) was fractionated into fractions of different apparent molecular weights by sequential ultrafiltration with decreasing molecular weight cut off (MWCO) filter sizes. Starting material was first freed from any particles by centrifugation for 15 min, 5,000 g. The fractions having an apparent molecular weight in the range of >1000 kDa, 300-1000 kDa, 100-300 kDa, 30-100 kDa, 10-30 kDa and 3-10 kDa, were prepared by sequential centrifugal ultrafiltration using VivaSpin 20 ultrafiltration units (Sartorius, Bohemia, NY, USA) of 1000 kDa, 300 kDa, 100 kDa, 30 kDa, 10 kDa or 3 kDa cut off, respectively. After each run, the flow through was used as input for the next filter. The retentates of all UF filters were washed with MilliQ water with 1000× the volume of the retentate to wash out lower molecular weight compounds.

The aggregative effect of the *Aloe* fractions towards *Staphylococcus aureus* and *Helicobacter pylori* was investigated. Samples of *Aloe vera* inner leaf juice, dialyzed juice and fractions D0 and D1 were also tested. 50 μl of a dilution of an *A. vera* sample in demi water and 50 μl of SYTO-24-labelled bacteria in 2×PBS were added to the wells of a 96 well transparent, flat-bottom polystyrene 96 wells microtiter plate (Greiner BioOne, Monroe, NC). The plates were incubated at 4° C. without shaking. Aggregation was checked with a fluorescence microscope after 16 hours and Maximal Aggregating Dilution (MAD) and Minimal Aggregating Concentration (MAC) were determined.

Results are presented in Table 3. The results show that the MAD value of the D0 fraction is significantly higher than the MAD value of the D1 fraction (about a factor 50). This means that the D0 fraction can be diluted many more times with retention of aggregating activity. This is partly due to the fact that the D0 fraction contains far more polysaccharides than the D1 fraction (97% versus 3%, respectively, of the total polysaccharides in the juice) and partly due to the fact that the polysaccharides in the D0 fraction are more active than those in the D1 fraction on a w/w basis (as illustrated by the lower MAC value for the D0 fraction). Moreover, the aggregates formed by the D0 fraction were much larger than the aggregates formed by the D1 fraction, indicating that the D0 fraction immobilizes more microorganisms and at lower concentrations than the D1 fraction. The more efficient aggregation and formation of larger aggregates by this D0 fraction result in neutralization of the microorganisms, since the aggregates result in more restrictive motion compared to single microbial cells, which may affect the motility of a microorganism when caught in aggregates. This will interfere with their potential to invade the mucosal barrier. Aggregates will also be cleared more easily from the system than single cells.

TABLE 3

| | S. aureus | | H. pylori | |
|---|---|---|---|---|
| | MAD | MAC (μg/ml) | MAD | MAC (μg/ml) |
| inner leaf juice | 2048 | 2.7 | 1024 | 5.5 |
| dialyzed juice | 1408 | 3.9 | 512 | 7.8 |
| >12 kDa fraction | | | | |
| D0 | 2048 | 2.7 | 768 | 5.9 |
| D1 | 14 | 9.8 | 12 | 11.7 |
| 3-10 kDa | 2 | n.d. | <1 | n.d. |
| 10-30 kDa | <1 | n.d. | <1 | n.d. |
| 30-100 kDa | 1024 | 1.3 | 1024 | 1.6 |
| 100-300 kDa | <1 | n.d. | <1 | n.d. |
| 300-1000 kDa | <1 | n.d. | <1 | n.d. |
| >1000 kDa | 1024 | 2.0 | 768 | 3.0 | n.d.: not detectable

For the ultrafiltration fractions, aggregating activity was mainly found in the 30-100 kDa fraction and in the >1000 kDa fraction. The MAC of the inner leaf juice was about 2-3× the MAC of the 30-100 kDa fraction, indicating that the purified 30-100 kDa fraction is several fold more potent than the original inner leaf juice when expressed on a weight basis. The 30-100 kDa fraction was also more potent than the >1000 kDa fraction. Both towards *S. aureus* and *H. pylori*, the 30-100 kDa fraction is the most potent *A. vera* fraction on a by weight basis.

Example 5 Aggregating Activity Towards *E. coli* and *C. albicans*

The 30-100 kDa fraction and the >1000 kDa fraction of Example 4 were also tested towards *E. coli* and the yeast *C. albicans*, starting with 50 μl active sample and 50 μl *E. coli* or *C. albicans* at OD 0.1. Aggregation was checked after 16 hours. Aggregating activity (MAD value) of active UF fractions are presented in Table 4. This shows that the 30-100 kDa fraction and the >1000 kDa fraction are also responsible for aggregating activity towards *E. coli* and *C. albicans*.

TABLE 4

| | MAD | |
|---|---|---|
| UF fraction | E. coli | C. albicans DSMZ 1386 |
| 30-100 kDa | 768 | 128 |
| >1000 kDa | 1024 | 768 |

Example 6 Polysaccharide Composition of Fractions with Aggregating Activity

The samples with aggregating capacity were lyophilized and neutral monosaccharides, galacturonic acid and glucuronic acid of the actives were determined by methanolysis at 80° C., followed by trifluoroacetic acid (TFA) hydrolysis at 120° C. for 75 minutes of the oligo- and polysaccharides into monosaccharides. Monosaccharides in the hydrolysates were determined by high pH anion-exchange chromatography with pulsed amperometric detection (HPAEC-PAD) quantification (Eurofins Food Testing Netherlands B.V., Heerenveen). The lower limit of detection of the sugars is about 0.05 mg/mL for each individual monosaccharide in these sample solutions.

The analysis showed that neutral fraction D0 contained polysaccharides mainly comprising mannose (about 95% w/w) with a small concentrations of glucose (about 3.5% w/w). The negatively charged fraction D1 contained mostly galactose (about 32%) and a significant amount of galacturonic acid (about 24% w/w). Mannose and arabinose each constituted approximately 15% w/w, based on the total saccharides in the D1 sample.

The polysaccharides of the most potent fractions of Examples 4 and 5, the 30-100 kDa fraction and the >1000 kDa fraction, were mainly comprised of mannose (more than 85% w/w), some glucose, galactose and some fucose. The most active fraction, the 30-100 kDa fraction, contained at least 90% w/w mannose, about 3% w/w glucose and about 1% w/w fucose. The mannose:glucose weight ratio of this fraction was 32. Thus, the polysaccharides in the D0 fraction, the 30-100 kDa fraction and the >1000 kDa fraction, which are responsible for the aggregating activity of *Aloe vera* inner leaf juice, comprised mainly mannose (more than 80% w/w), some glucose (3-4% w/w) and only small amounts of other carbohydrates.

TABLE 5

| | carbohydrate distribution (% w/w) | | | | |
|---|---|---|---|---|---|
| | >12 kDa | 30-100 kDa | >1000 kDa | D0 | D1 |
| Fucose | 0.9 | 1.1 | 1.0 | 1.1 | 0.0 |
| Arabinose | 0.9 | 0.4 | 1.0 | 0.0 | 15.1 |
| Rhamnose | 0.0 | 0.0 | 0.0 | 0.0 | 1.2 |
| Galactose | 1.9 | 0.7 | 2.9 | 0.6 | 32.6 |
| Glucose | 3.8 | 3.0 | 3.9 | 3.4 | 1.2 |
| Xylose | 0.5 | 0.4 | 1.0 | 0.0 | 7.0 |
| Mannose | 90.6 | 94.1 | 89.3 | 94.9 | 14.0 |
| Galacturonic acid | 0.9 | 0.4 | 1.0 | 0.0 | 24.4 |
| Glucuronic acid | 0.5 | 0.0 | 0.0 | 0.0 | 4.7 |

Example 7 Preparation of D0 and D1 Fractions of *Aloe* Batch 21

A new batch (batch 21) of 10× concentrated *Aloe vera* inner leaf juice (ACTIValoe® *Aloe vera* Gel 10X-D, AloeCorp, Harlingen, TX, USA) was used to a prepare D0 fraction (B21 D0 fraction) and a D1 fraction (B21 D1 fraction) as described before in Example 3.

Example 8 Fractionation of B21 D0

The B21 D0 fraction was subsequently fractionated into fractions of different apparent molecular weights by sequential ultrafiltration with decreasing molecular weight cut off (MWCO) filter sizes as described in Example 4. This time, the 30-100 kDa fraction, was subfractioned into a 50-100 kDa and a 30-50 kD fraction for further study.

Example 9 Aggregation of B21 D0, D1 and D0-UF Fractions

The aggregative effect of theB21 *Aloe* fractions towards *Staphylococcus aureus* was investigated. Samples of *Aloe vera* inner leaf juice, dialyzed juice and fractions D0 and D1 were also tested. 50 µl of a dilution of an *A. vera* sample in demi water and 50 µl of SYTO-24-labelled bacteria in 2×PBS were added to the wells of a 96 well transparent, flat-bottom polystyrene 96 wells microtiter plate (Greiner BioOne, Monroe, NC). The plates were incubated at 4° C. without shaking. Aggregation was checked with a fluorescence microscope after 16 hours and Maximal Aggregating Dilution (MAD) and Minimal Aggregating Concentration (MAC) were determined.

Results are presented in Table 6 and show that the MAD value of the D0 fraction is significantly higher than the MAD value of the D1 fraction (about a factor 250). This means that the D0 fraction can be diluted many more times with retention of aggregating activity. This is partly due to the fact that the D0 fraction contains far more polysaccharides than the D1 fraction (98.5% versus 1.5%, respectively, of the total polysaccharides in the juice) and partly due to the fact that the polysaccharides in the D0 fraction are more active than those in the D1 fraction on a w/w basis (as illustrated by the lower MAC value for the D0 fraction). Moreover, the aggregates formed by the D0 fraction were much larger than the aggregates formed by the D1 fraction, indicating that the D0 fraction immobilizes more microorganisms and at lower concentrations than the D1 fraction. The more efficient aggregation and formation of larger aggregates by this D0 fraction result in neutralization of the microorganisms, since the aggregates result in more restrictive motion compared to single microbial cells, which may affect the motility of a microorganism when caught in aggregates. This will interfere with their potential to invade the mucosal barrier. Aggregates will also be cleared more easily from the system than single cells.

TABLE 6

| | S. aureus | |
|---|---|---|
| Batch 21 (B21) | MAD | MAC (µg/ml) |
| inner leaf juice | 1024 | 4 |
| dialyzed juice | 1024 | 4 |
| >12 kDa fraction | | |
| D0 | 2048 | 1.6 |
| D1 | 8 | 6 |
| D0 <3 kDa | <8 | |
| D0 3-10 kDa | <2 | |
| D0 10-30 kDa | <2 | |
| D0 30-50 kDa | 8 | n.d. |
| D0 50-100 kDa | 1024 | 1.25 |
| D0 100-300 kDa | 4 | n.d. |
| D0 300-1000 kDa | <2 | |
| D0 >1000 kDa | <2 | | n.d.: not detectable

For the ultrafiltration fractions, aggregating activity was mainly found in the 50-100 kDa fraction. The very viscous >1000 kDa fraction showed less activity than the 50-100 kDa fraction, making it less interesting as an aggregating agent. The MAC of the inner leaf juice was about 3× the MAC of the 50-100 kDa fraction, indicating that the purified 50-100 kDa fraction is several fold more potent than the original inner leaf juice when expressed on a weight basis.

Example 10 Polysaccharide Composition of Fractions with Aggregating Activity The samples with aggregating capacity were lyophilized and polysaccharide composition was determined (Eurofins Food Testing Netherlands B.V., Heerenveen) as described in Example 6 above. Data analysis showed (Table 7) that the batch 21 comprised about 28% w/w mannose and 70% w/w glucose. The B21 D0 fraction and the B21 D0 50-100 kDa fraction comprised 95-96% w/w mannose and 2-3% w/w glucose. The acemannan fraction comprised about 85% w/w mannose and about 8% w/w glucose. The other monosaccharide were 1% or less. All percentages based on total polysaccharides. The batch21 aggregating fractions clearly have more mannose and less glucose in their polysaccharide fractions than acemannan.

TABLE 7

| | carbohydrate distribution (% w/w) | | | |
|---|---|---|---|---|
| | batch 21 | D0 | D0 50-100 kDa | acemannan |
| Galactose | 1 | 2 | 2 | 2 |
| Glucose | 70 | 2 | 3 | 8 |
| Mannose | 28 | 95 | 95 | 85 |

Example 11 Treatment of Mastitis 25 cows were treated with a pH neutral gel comprising a composition according to the invention. The gel comprising 2 gram/l polysaccharides, 2% w/w Carbopol (Carbopol™ 1382, Lubrizol, Cleveland, US) and 15% w/w 1,2 propylene glycol was injected in the teat of a cow using a plastic udder injector. Mastitis was identified by visual inspection of the animals by the farmer. Indications for mastitis were redness or swelling of the udder or the teat, combined with general malaise of the cow. If mastitis was observed, 5 to 10 ml of the gel was applied in the teat immediately after milking. This was repeated for three days. Results were equal to or even better than with standard antibiotic treatment. After treatment with the composition according to the invention, recurrency of mastitis seemed reduced compared to antibiotic treatment.

Example 12 Treatment of Metritis

Cows showing signs of endometritis, i.e. general malaise or dullness, uterine effluent or elevated temperature, were treated by flushing the uterine with generous amounts of a gel comprising the composition according to the invention. The gel comprising 1.5 gram/l polysaccharides, 3% w/w xanthan gum (Xanthanal 11K, PKelco, France) and 0.3% w/w caprylyl glycol (1,2-octanediol) (Dermosoft Octiol, Dr. Straetmans Chemische Produkte GmbH, Hamburg. Germany) was used for uterine flushing twice a day for five days. A significant reduction of post-partum infection was observed in comparison to no flushing. Results were comparable to standard antibiotic flushing results.

The invention claimed is:

1. A composition comprising polysaccharides derivable from *Aloe vera*, the composition comprising:
   80-100% w/w mannose; and
   0-5% w/w glucose by weight of total polysaccharides,
   wherein the composition is capable of an aggregating activity towards microorganisms if contacted therewith,
   wherein the composition is obtained as flow through fraction not bound to an anion exchange column at pH 7, and
   wherein the polysaccharides in the composition have an apparent molecular weight in the range of 30-100 kDa, as determined by ultrafiltration.

2. The composition of claim 1, wherein the polysaccharides in the composition have an apparent molecular weight in the range of preferably 50-100 kDa, as determined by ultrafiltration.

3. The composition of claim 1, wherein the weight ratio of mannose:glucose is in the range of 25 to 35.

4. The composition of claim 1, the composition further comprising 0-5% w/w galactose or 0-5% w/w fucose, by weight of total polysaccharides.

5. The composition of claim 1, wherein the composition comprises from 0.5-10 mg/ml polysaccharides.

6. The composition of claim 1, wherein the composition further comprises *Aloe vera* extracts, antibiotics, chitosan, nutrients or vitamins.

7. The composition of claim 1, wherein the composition is formulated as a cream, drops, gel, liquid, lotion, paste, shampoo, spray, tonic, capsule, lozenge, powder or tablet.

8. A method for treatment or prevention of an infection by a microorganism in a human or animal body, comprising the steps of:
   administering to a human or animal subject, a composition comprising:
      80-100% w/w mannose; and
      0-5% w/w glucose by weight of total polysaccharides,
      wherein the composition is capable of an aggregating activity towards microorganisms if contacted therewith,
      wherein the composition is obtained as flow through fraction not bound to an anion exchange column at pH 7, and
      wherein the polysaccharides in the composition have an apparent molecular weight in the range of 30-100 kDa, as determined by ultrafiltration.

9. The method of claim 8, wherein the infection is in livestock, pets, sports animals or cattle.

10. The method of claim 8, wherein microorganism is a bacterium, fungus, or virus.

11. The method of claim 8, wherein the microorganism is selected from the group consisting of *Bacillus, Bacteroides, Clostridium, Enterococcus, Escherichia, Listeria, Neisseria, Pseudomonas, Salmonella, Staphylococcus, Streptococcus, Yersinia, Aspergillus* and *Candida*.

12. The method of claim 8, wherein the microorganism is selected from the group consisting of *C. albicans, S. aureus, E. coli* and *H. pylori*.

13. The method of claim 8, wherein the composition is formulated as a cream, drops, gel, liquid, lotion, paste, shampoo, spray, tonic, capsule, lozenge, powder or tablet.

14. The method of claim 8, wherein the composition reduces or prevents microbial colonisation in the human or animal subject.

* * * * *